United States Patent [19]

Ciomo

[11] 4,452,724
[45] Jun. 5, 1984

[54] ALKYL VANADATE COLOR IMPROVEMENT

[75] Inventor: George C. Ciomo, Hastings-on-Hudson, N.Y.

[73] Assignee: Stauffer Chemical Company, Westport, Conn.

[21] Appl. No.: 426,551

[22] Filed: Sep. 29, 1982

[51] Int. Cl.$^3$ ............................................... C07F 9/00
[52] U.S. Cl. ................................................... 260/429 R
[58] Field of Search .................................... 260/429 R

[56] References Cited

U.S. PATENT DOCUMENTS

| | | | |
|---|---|---|---|
| 1,133,961 | 3/1915 | Hess | 260/429 R |
| 2,220,041 | 10/1940 | Hill | 260/429 R |
| 2,257,009 | 9/1941 | Hill | 260/429 R |
| 3,652,617 | 3/1972 | Termin et al. | 260/429 R |
| 3,657,295 | 4/1972 | McCoy | 260/429 R |
| 3,920,751 | 11/1975 | Chabardes et al. | 260/429 R |
| 3,987,074 | 10/1976 | Haase et al. | 260/429 R |
| 4,014,911 | 3/1977 | Muntz et al. | 260/429 R |
| 4,014,912 | 3/1977 | Muntz et al. | 260/429 R |
| 4,351,775 | 9/1982 | Magee | 260/429 R |

Primary Examiner—Helen M. S. Sneed
Attorney, Agent, or Firm—Richard P. Fennelly

[57] ABSTRACT

The color of alkyl vanadate compounds that have become discolored is improved by treating the vanadates with a nitrogen oxide oxidant to achieve the color improvement.

10 Claims, No Drawings

ALKYL VANADATE COLOR IMPROVEMENT

BACKGROUND OF THE INVENTION

1. Field of the Invention

The present invention relates to the color improvement of alkyl vanadates.

2. Description of the Prior Art

Various methods are known for the preparation of alkyl vanadates. U.S. Pat. No. 4,014,912 to R. L. Muntz et al. describes reaction of vanadium oxytrichloride with an alcohol in the presence of ammonia and a hydrocarbon solvent with the later addition of dimethyl sulfoxide. The reaction is conducted under an inert gas atmosphere to prevent decomposition of the product. A variation of this process, in which an amide is added, rather than dimethyl sulfoxide, is described in U.S. Pat. No. 4,014,911 to R. L. Muntz et al. In this patent it is suggested that a stream of inert gas be passed through the reaction mixture to sweep out a portion of the hydrogen chloride by-product released by the reaction.

Alkyl vanadates are formed by reaction of vanadium pentoxide and an alkyl alcohol in a process described in U.S. Pat. No. 3,657,295 to D. R. McCoy. Once again, this patent indicates use of an inert atmosphere to prevent decomposition of the product.

In U.S. Pat. No. 3,987,074 to R. Haase et al. alkyl vanadates are described as being prepared by reaction of vanadium pentoxide and an alcohol in the presene of a particular orthoester to assist in the removal of by-product water. This patent indicates that vanadium pentoxide reagent remaining after the reaction can be regenerated and restored to full reactivity by thermal treatment, e.g., at 300°–400° C., under air or oxygen.

Color improvement of alkyl vanadate compounds by treating them with a stream of oxygen-containing gas is suggested in pending U.S. Ser. No. 416,818, filed Sept. 13, 1982.

SUMMARY OF THE PRESENT INVENTION

The present invention is a process for color improvement of alkyl vanadate compounds which have at least partially decomposed. It comprises treating the alkyl vanadate with a nitrogen oxide oxidant to achieve the color improvement.

DESCRIPTION OF THE PREFERRED EMBODIMENTS

Alkyl vanadates, which have become discolored due to chemical decomposition, can have their color improved by treatment with a nitrogen oxide oxidant under conditions which result in said color improvement.

Various substances can be used to supply the nitrogen oxide oxidant to the discolored or darkened alkyl vanadate. For example, nitric acid can be used. Alternatively, a nitrogen oxide gas, such as nitrogen dioxide, can be employed.

The amount of nitrogen oxide oxidant-containing substance that can be employed in accordance with the present invention to achieve the desired color improvement can be quite small in comparison to the amount of vanadate. Generally amounts of from about 0.01% to about 2%, by weight, of the vanadate are sufficient. The contacting of vanadate and the oxidant containing substance is preferably carried out at elevated temperature (e.g., from about 90° C. to about 120° C.) in order to achieve color improvement over an extended length of time (i.e., enhanced color stability). Nitrogen dioxide, as a nitrogen oxide-containing gas, is preferred since it confers superior color stability on the treated vanadate compositions.

In those cases in which addition of a dark precipitate is formed by adding the nitrogen oxide oxidant (e.g., nitric acid), filtration of the vanadate to remove the precipitate can be employed. In cases in which the vanadate becomes more highly colored than desired when sparged with a nitrogen oxide-containing gas, the color can be restored to its desired, less colored state by sparging with an inert gas, such as nitrogen.

This invention is further illustrated by the Examples which follow.

EXAMPLE 1

Black colored triisobutyl vanadate (25 cc.), obtained by reacting $V_2O_5$ and isobutanol in heptane solvent using a urea/ammonium carbonate catalyst, was placed in a 30 cc. bottle. A droplet of 70% nitric acid was added to the vanadate at a temperature slighly above room temperature (i.e., about 30°–40° C.). The bottle was closed and shaken. No color improvement was noticed at that time. Five days later, the sample was again examined. The color of the triisobutyl vanadate had improved to dark yellow. A fluffy, dark olive sediment was observed on the bottom of the bottle.

COMPARATIVE EXAMPLES 2–9

The procedure described in Example 1 was repeated with the compounds listed below. No improvement in color of the vanadate was noted either at the time of the procedure or later:

| Example No. | Added Compound |
| --- | --- |
| 2 | Benzoic acid |
| 3 | Benzoyl peroxide |
| 4 | Acetic anhydride |
| 5 | Sodium bisulfite |
| 6 | Potassium persulfate |
| 7 | Potassium permanganate |
| 8 | Sodium perchlorate |
| 9 | Sodium nitrite |

EXAMPLE 10

Black colored triisobutyl vanadate (40 cc.) was heated in an open beaker equipped with a magnetic stir-bar to 100°–110° C. A droplet of 70% nitric acid was added at this temperature. The color of the liquid turned instantly to light yellow. A very small amount of a fine, black precipitate was also formed. The treated triisobutyl vanadate was poured into two 30 cc. bottles. One bottle was placed in a box while the other was placed on an open shelf. Both of these samples remained light yellow in color after storage for 60 days.

COMPARATIVE EXAMPLES 11–20

The procedure of Example 10 was repeated using the following compounds as additives:

| Example No. | Added Compound |
| --- | --- |
| 11 | 30% Hydrogen peroxide |
| 12 | Benzoyl peroxide |
| 13 | 65% $H_2SO_4$ oleum |
| 14 | Nitromethane |
| 15 | Nitrobenzene |

-continued

| Example No. | Added Compound |
| --- | --- |
| 16 | Sodium nitrite |
| 17 | Sodium perchlorate |
| 18 | Potassium persulfate |
| 19 | 2,2-dimethoxy propane |
| 20 | Air |

An improved color was initially obtained in all cases, however, after 60 days storage all treated samples turned either dark brown or black.

EXAMPLE 21

Black colored triisobutyl vanadate (500 gm.) was heated in a one-liter, three-necked flask, equipped with magnetic stir-bar and thermometer. A nitrogen blanket was provided above the surface of the liquid to prevent a color change due to air contact. At 100° C., 0.05 cc (or one droplet) of 70% nitric acid was added to the flask. This corresponds to 0.01 wt. % nitric acid (on a 100% basis) added to the vanadate. The color of the vanadate changed to light yellow. A sample of the vanadate was withdrawn.

Nitric acid addition was resumed, and another sample, containing about 0.06 wt. % nitric acid, was prepared and removed.

Both samples were examined periodically. A darkening was noticed after two weeks in the first sample, and it turned brown after 60 days. The second sample preserved the light yellow color for the entire 60 day period.

EXAMPLE 22

Black triisobutyl vanadate (300 gm.) was placed in a 500 ml. three-neck flask equipped with a sintered glass sparging tube, magnetic stir-bar, and a thermometer. A 5% sodium hydroxide trap was installed on the vent line.

The material was heated to 110° C. and nitrogen dioxide gas was added through the sparging tube into the liquid vanadate. When 0.7 gm. of nitrogen dioxide had been added, the color of the vanadate turned light yellow. No precipitate was generated.

The liquid was sparged with nitrogen for 15 minutes at 100° C.

The nitrogen dioxide sparged product exhibited the same color stability as the second sample of nitric acid treated material described in Example 21, i.e., it retained its light yellow color for 60 days.

EXAMPLE 23

The procedure described in Example 22 was repeated using an excess of nitrogen dioxide. The yellow color of the liquid in the flask turned orange and then red. About 7% nitrogen dioxide gas appeared to reach the caustic trap. The flask was weighed and showed a gain in weight equal to the amount of nitrogen dioxide added.

The contents of the flask were sparged for 30 minutes with nitrogen. The color turned to orange and then to dark yellow. At the end of the sparging, the flask had regained it original weight indicating that the nitrogen dioxide had been substantially removed.

A sample of the product from this Example showed color stability comparable to the product treated as in Example 22.

EXAMPLE 24

The procedure described in Example 22 was repeated using nitric oxide (NO) instead of nitrogen dioxide ($NO_2$). The dark colored triisobutyl vanadate turned light yellow as soon as the treatment with NO was begun. After three weeks the light yellow color had not appreciably darkened.

The foregoing Examples illustrate certain preferred embodiments of the present invention and should not be construed in a limiting sense. The scope of protection that is sought is set forth in the claims which follow.

What is claimed:

1. A process for the color improvement of alkyl vanadates which comprises treating the alkyl vanadate with an effective amount of a nitrogen oxide oxidant to achieve the color improvement.

2. A process as claimed in claim 1 wherein the vanadate is treated with nitric acid.

3. A process as claimed in claim 1 wherein the vanadate is treated with a nitrogen oxide oxidant-containing gas.

4. A process as claimed in claim 1 wherein the vanadate is treated with nitrogen dioxide.

5. A process as claimed in claim 1 wherein the vanadate is treated with nitric oxide.

6. A process as claimed in claim 1 wherein the vanadate is treated with from about 0.01% to about 2%, by weight, of a substance containing the nitrogen oxide oxidant.

7. A process as claimed in claim 1 wherein the treating takes place at a temperature of from about 90° C. to about 120° C.

8. A process as claimed in claim 1 wherein the vanadate is treated with from about 0.01% to about 2%, by weight, of a substance containing the nitrogen oxide oxidant at a temperature of from about 90° C. to about 120° C.

9. A process as claimed in claim 4 wherein the vanadate is treated with from about 0.01% to about 2%, by weight of the nitrogen dioxide.

10. A process as claimed in claim 9 wherein the treatment takes place at from about 90° C. to about 120° C.

* * * * *